United States Patent [19]

Katz et al.

[11] Patent Number: 4,502,150
[45] Date of Patent: Feb. 26, 1985

[54] ARTIFICIAL LARYNX

[75] Inventors: Philip Katz, Princeton Junction; Henry S. Brenman, Cinnaminson, both of N.J.; Louis D. Lowry, Villanova; Harold Schwartz, King of Prussia, both of Pa.

[73] Assignee: Thomas Jefferson University, Philadelphia, Pa.

[21] Appl. No.: 428,848

[22] Filed: Sep. 30, 1982

Related U.S. Application Data

[63] Continuation of Ser. No. 249,140, Mar. 30, 1981, Pat. No. 4,473,905.

[51] Int. Cl.³ .............................................. A61F 1/20
[52] U.S. Cl. .................................................... 381/70
[58] Field of Search ............. 179/1 AL, 121 C; 3/1.3; 381/70

[56] References Cited

U.S. PATENT DOCUMENTS

| | | | |
|---|---|---|---|
| 2,093,453 | 9/1937 | Kellotat | 3/1.3 |
| 2,862,209 | 12/1958 | Cooper | 179/1 AL |
| 3,072,745 | 1/1963 | Barney | 179/1 |
| 3,084,221 | 4/1963 | Cooper | 179/1 AL |
| 3,291,912 | 12/1966 | Flanagan | 179/1 |
| 3,508,000 | 4/1970 | Snyder | 179/1 |
| 3,766,318 | 10/1973 | Webb | 179/1 |
| 3,914,550 | 10/1975 | Cardwell, Jr. | 179/1 |
| 4,039,756 | 8/1977 | Burtschi | 179/1 AL |
| 4,223,411 | 9/1980 | Schoendorfer | 3/1.3 |

FOREIGN PATENT DOCUMENTS

| | | |
|---|---|---|
| 208505 | 4/1960 | Austria . |
| 58077 | 8/1982 | European Pat. Off. . |
| 2507704 | 9/1976 | Fed. Rep. of Germany . |
| 2515006 | 10/1976 | Fed. Rep. of Germany . |
| 2818853 | 11/1978 | Fed. Rep. of Germany . |
| 1213521 | 11/1970 | United Kingdom . |

OTHER PUBLICATIONS

Medorobics, Inc., publication distributed at International Association for Laryngectomees Annual Convention, Wichita, Kansas, summer 1982.
"A Self-Contained Intra-Oral Artificial Larynx", by Kenneth J. Stern, Bioengineering Senior Design Project–BE495, Fall 1978, Spring 1979.
"A Self-Contained Intra-Oral Electro-Larynx" Progress Report Dec., 1979, Kenneth Stern, Bioengineering 495 Senior Design Project.
Goode et al., "An Intraoral RF Powered Artificial Larynx" Proceedings of the 23rd Annual Conference on Engineering in Medicine & Biology–Wash., D.C., 1970, vol. 12, p. 335.
"An Electrical Vocal System", L. O. Schott, Bell Laboratories Record, Dec. 1950, pp. 549–555.
"An Electrical Analog of the Vocal Tract", K. N. Steven et al., Journal of the Acoustical Society of America, vol. 25, No. 4, Jul. 1953, pp. 734–742.
"The Calculation of Vowel Resonances and an Electrical Vocal Tract", H. K. Dunn, Journal of the Acoustical Society of America, vol. 22, No. 6, Nov. 1950, pp. 740–753.

(List continued on next page.)

*Primary Examiner*—Gene Z. Rubinson
*Assistant Examiner*—W. J. Brady
*Attorney, Agent, or Firm*—Woodcock Washburn Kurtz Mackiewicz & Norris

[57] ABSTRACT

The present invention provides a completely self-contained intraoral larynx comprising a power source, tongue activated controls, power saving signal generation circuitry, acoustic and audio amplifiers, and an intra-oral speaker. These components are contained within an otherwise conventional denture or dental prosthesis. The device produces a high amplitude sound while minimizing current drain from the power source. Laryngectomized patients require only short term training by a speech pathologist to use this device. Intelligible speech is usual within an hour of such training, and facility rapidly improves. The psychological barriers, post-operative physical limitations, aesthetic concerns and limited gestural communication traditionally associated with the use of extra-oral larynges is eliminated by the present invention.

4 Claims, 3 Drawing Figures

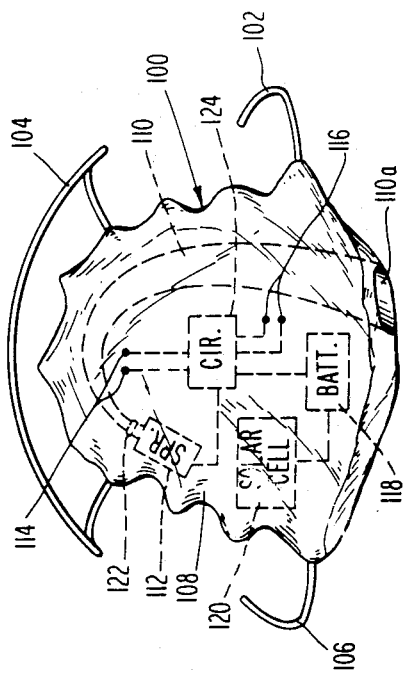
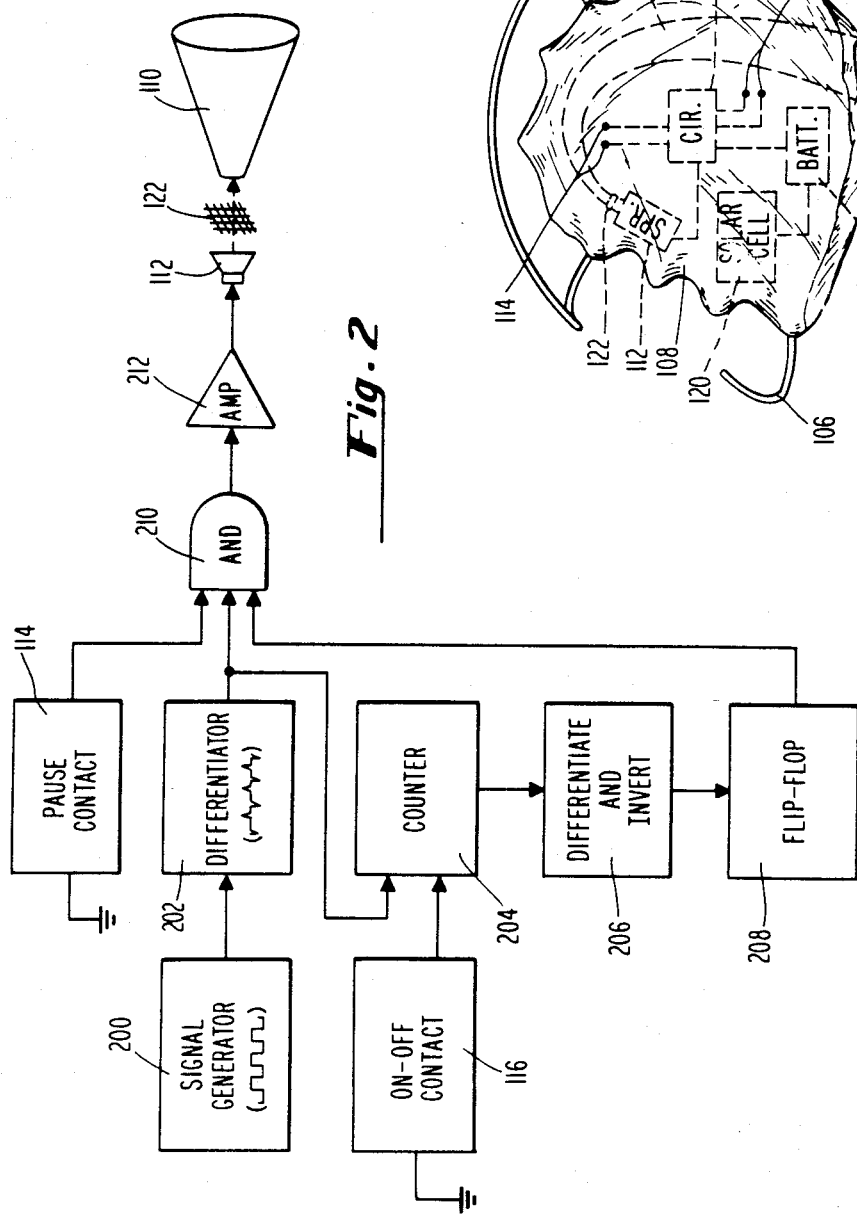

ARTIFICIAL LARYNX

This is a continuation of application Ser. No. 249,140, filed 3/30/81, now U.S. Pat. No. 4,473,905.

BACKGROUND

The present invention relates to the field of sound producing prosthetic devices for use by laryngectomized patients.

Many devices have been suggested for providing speech capability to laryngectomized patients. One approach involves the provision of a mechanical or electromechanical device to create pitches or tones which are modulated to produce speech. In Richard L. Goode's review entitled "Artificial Laryngeal Devices In Post-Laryngectomy Rehabilitation", which appeared in *The Laryngoscope* (pages 677–689, 1974), two basic types of artificial larynges, transcervical and transoral larynges, are disclosed. Transcervical larynges are electronic, hand-held, battery-powered, vibrating devices that are placed on the neck to produce voice. While transcervical devices have experienced considerable commercial success, they must be hand held on the neck whle speaking, produce an "electronic" type of speech, leak unwanted sound from the neck, need battery changes, and require a place on the neck that will allow efficient transfer of sound vibrations. Transoral laryngeal devices are electronic or pneumatic devices in which the sound enters the mouth through a tube. While such units produce a loud sound and may be used in early post-operative stages by patients with thick neck tissue who cannot use transcervical devices, transoral devices are noticeable in use, require placement in the mouth, and are prone to saliva blockages. Additionally, transoral devices may result in articulation which is disturbed by the placement of the tube near the tongue and lips, this results in speech which is less intelligible than that produced by transcervical devices.

The desirability of including all of the operative components of an artificial larynx on an intraoral prothesis has long been recognized. See for example U.S. Pat. No. 2,862,209, Col. 1, lines 61–64. Unfortunately, the art has heretofore failed to disclose any complete intraoral device.

One early attempt at an "intraoral" device is the "Tait larynx". In 1974 Goode, supra. described the Tait larynx, "no longer manufactured", as comprising an intra-oral earphone attached to a patient's denture or dental retainer, an external power source, external oscillator and external on-off switch. In the Tait device a wire was passed from the intraoral earphone to these external components. While the sound produced by the Tait device is at least comparable to that produced by other transoral larynges, the presence of a wire coming out of the user's mouth makes the Tait device unacceptable to most laryngectomees. For a disclosure of a similar transoral device see U.S. Pat. No. 2,862,209.

Pichler eliminated any need for transoral wiring by suggesting that a wireless induction system could be used to transmit sound from a pocket oscillator driven primary coil worn around the neck to an intraoral secondary coil associated with an intraoral earphone. However, Pichler's device has apparently never been placed on the market. See Goode, supra.

In an attempt to improve upon the Pichler device, Goode suggests that a miniature pulse generator capable of being mounted on a denture or dental retainer can be used to drive a small, waterproof, low impedance, modified insert earphone. Power is provided to the pulse generator by a handheld, external radio frequency generator operating at 100 kHz and using a 15-volt rechargeable battery pack, carried in the pocket, with a battery drain of 780 mW. When the transmitter is held to the cheek, the transmitter coil lies about 1.5 cm from a miniature, tuned receiving coil in the denture.

A wireless electro-larynx consisting of a receiver/speaker concealed in an ordinary denture or prosthesis, and an external transmitter worn under the patient's clothing has been suggested by Zwitman et al. See "Development and Testing of an Intraoral Electrolarynx for Laryngectomy Patients", Zwitman et al, *Journal Of Speech And Hearing Disorders*, XLIII, 263–269 (May, 1978). In the Zwitman et al device, a 1 millimeter thick receiver is housed in the center of the denture and surrounded by a receiving coil which is used to pick up an incoming differentiated transmitter-generated pulse which is then amplified. This amplified signal is used to change the state of a bistable multivibrator circuit, which then activates an astable multivibrator. This astable multivibrator then begins to oscillate at a repetition rate (fundamental frequency) of 70 Hz to produce an audible buzz. Current is permitted to pass through the receiver for only 0.3 msec periods, which are long enough to facilitate the generation of intelligible speech, while conserving battery life. A plastic tube is attached to the speaker of the Zwitman et al device which extends medially and slightly upward past the mid-line of the palate to a point just short of the opposite side of the dental prosthesis. This tube is intended to transmit sounds to the posterior region of the oral cavity to provide maximum resonance, and to prevent the tongue from occluding the speaker aperture. Two rechargeable batteries are used to power the receiver/speaker for up to five continuous hours. Since the standby current drain is low, Zwitman et al reported that intermittent use of the unit permits it to function for an entire day before recharging is necessary.

In "A Modified Intraoral Electro-larynx", McRae et al, *Archives of Otolaryngology* 105: 360–361, 1979, and in "The Design of a Wireless-Controlled Intraoral Electro-larynx", Knorr et al, *Journal of Bioengineering* 1: 165–171, 1977, other designs of intraoral electro-larynges are disclosed.

More recently, in work conducted by Mr. Kenneth Stern, a self-contained, intra-oral artificial larynx has been suggested, and Stern's described circuitry breadboarded. This circuit generates a squarewave of 125 Hz which is used as a clock for a five stage binary counter. Outputs of the counter are logically interconnected through exclusive-or's, amplified, and used to energize a speaker to produce a buzz. By using bi-lateral switches, most of the circuitry is not powered in order to extend battery life.

Stern has suggested the desirability of providing a tongue operated switch for power control, and of providing a speaker housed in the mouth which produces varied output frequencies which simulate changes of pitch; however Stern has failed to provide designs for these components.

As seen from the above, the desirability of providing a completely self-contained, intraoral artificial larynx has long been recognized. Nonetheless, there is a long felt need for a simple, intraoral, tongue-controlled larynx which may function without recharging over extended periods of time, and which facilitates the generation of clearly audible speech.

SUMMARY OF THE INVENTION

The present invention provides a novel, completely self-contained intraoral artificial larynx. This larynx is an ultra thin, miniature device which may be mounted on or within a dental appliance and is wholly contained in the mouth. Based on an estimate of 3 hours per day of continuous speaking, the larynx of the present invention may be used for up to 30 days without battery replacement or recharging.

The preferred embodiment of the present invention comprises a power source, tongue activated controls, power saving signal generation circuitry, an audio amplifier, an intraoral speaker, and an acoustic amplifier which is tuned to the output of that speaker. Power saving signal generation circuitry is designed to produce a high amplitude signal which drives the speaker to produce an "audio flicker". In the preferred embodiment, the tongue activated controls comprise contacts located on the palate which may be touched by the tongue to activate, deactivate, or temporarily disable the artificial larynx. In order to prevent accidental activation or deactivation, the on-off contact must be touched for preselected periods of time to produce the desired activation or deactivation of the device. Occlusion of the speaker with saliva or water is prevented by locating the speaker at one end of an acoustic horn, encapsulating the speaker, and by disposing a mesh between the speaker and the horn which is effective to prevent fouling of the speaker with any liquid which has successfully passed through the horn. The mesh causes no significant sound attenuation.

Laryngectomized patients would require minimal short term training to use the device of the present invention, and this device can be conveniently worn for extended periods of time. Unlike prior art devices which have relied upon extraoral components, the device of the present invention is worn entirely within the mouth and is incapable of visual detection. A unique combination of tongue controls for permitting convenient intermittent use, novel power saving circuitry, and tuned acoustic amplification permit the device of the present invention to be used for far longer periods between battery replacement or recharge then has heretofore been possible.

In an alternate embodiment of the present invention, the artificial larynx is completely sealed, and includes a solar cell for recharging a self-contained power source, such as a rechargeable battery. In this embodiment, the larynx is made so that the power source may be recharged by placing it under a light source when it is not being worn.

Accordingly, a primary object of the present invention is the provision of an entirely self-contained, intraoral larynx.

A further object of the present invention is the provision of an intraoral larynx which is entirely tongue controlled.

A further object of the present invention is the provision of a tongue controlled intraoral switching device.

Another aim of the present invention is the provision of power saving signal generation circuitry for use in driving an artificial larynx.

A further object of the present invention is the provision of an artificial larynx which resists fouling by saliva or water.

A further aim of the present invention is the provision of an artificial larynx having a tuned acoustic amplifier for maximizing the amplitude of sound generated by the electronic tone generator.

These and further objects of the present invention will become apparent from the following, more detailed description.

BRIEF DESCRIPTION OF THE DRAWINGS

FIG. 1 is a diagrammatic plan view of the top surface of a preferred embodiment artificial larynx, diagrammatically illustrating the speaker, battery, solar cell, acoustic horn, mesh and tongue contacts which are contained within an otherwise conventional dental prosthesis;

FIG. 2 is a block diagram illustrating the operative components of the preferred embodiment artificial larynx of the present invention;

DESCRIPTION OF THE PREFERRED EMBODIMENTS

Figure 3:
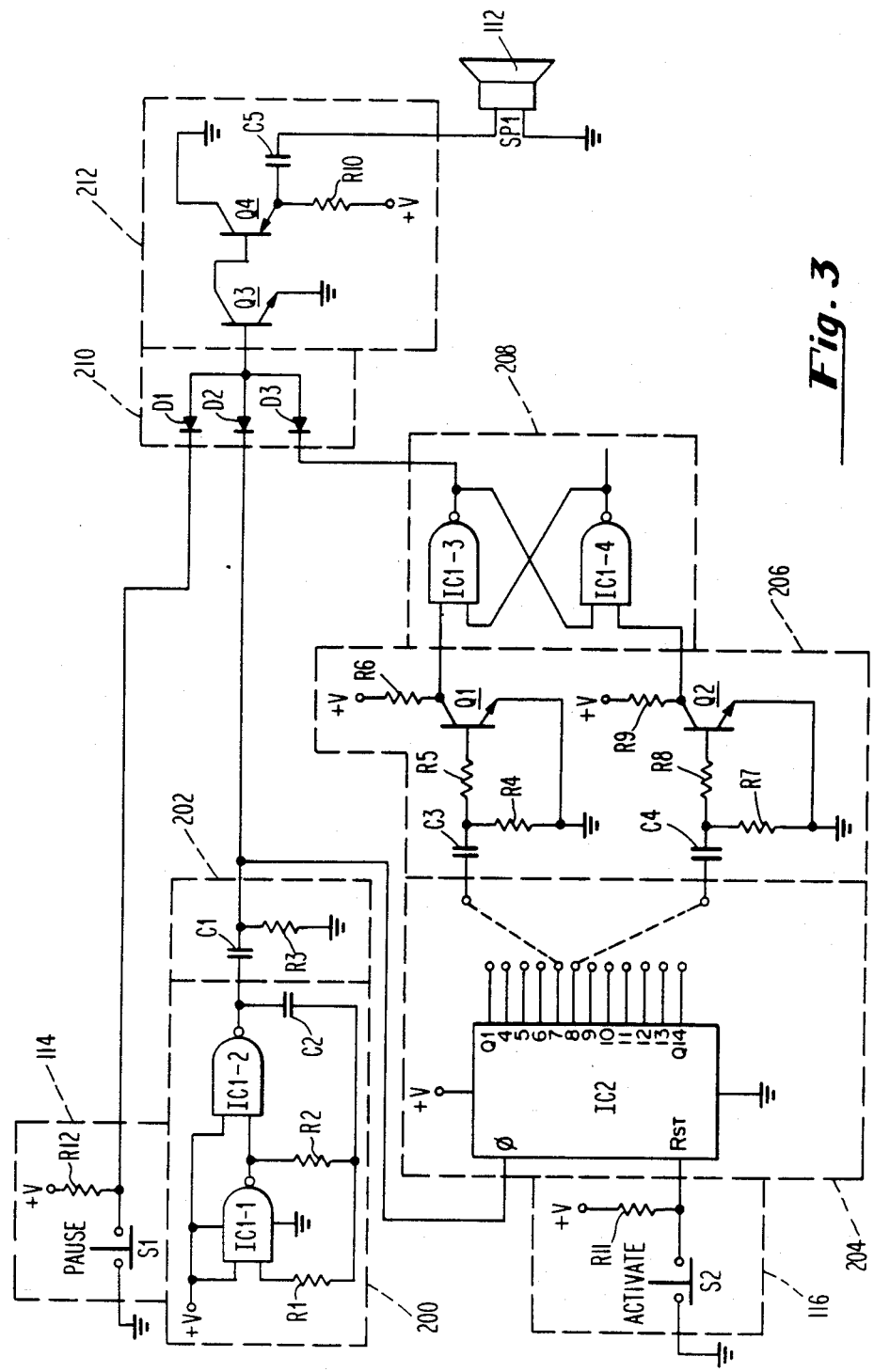
FIG. 3 is a circuit diagram of the preferred embodiment represented in FIG. 2.

While specific forms of the present invention have been selected for the purposes of illustration, one of ordinary skill in the art will recognize that various departures may be made to the examples set forth herein without departing from the scope of the present invention, which is defined more particularly in the appended claims.

The intraoral artificial larynx of the present invention generally comprises a prosthetic means for mounting the larynx within the oral cavity, a power source mounted on the prosthetic means, signal generation means mounted on the prosthetic means for generating preselected electrical signals, and speaker means mounted on the prosthetic means for converting said signal into acoustic energy. Referring now to FIG. 1, the prosthetic means, designated generally 100, will be seen to generally comprise a conventional palatal denture or dental prosthesis. Such a prosthesis usually comprising means for anchoring the prosthesis in the mouth cavity, such means in FIG. 1 being dental wires 102, 104 and 106. The body 108 of the dental prosthesis is formed from conventional dental prosthetic materials, such as an acrylic polymer, which is shaped to fit comfortably against the roof of the wearer's mouth. This body is preferably formed to encapsulate all of the electrical components of the preferred embodiment larynx, and is molded to contain an acoustic horn 110 which is the preferred acoustic amplification means for amplifying acoustic energy generated by the aforementioned speaker means. As shown in FIG. 1, the preferred acoustic horn 110 is arcuate, having its minimum diameter at its juncture with speaker 112 and its maximum diameter at its terminus 110a at the rear of the dental prosthesis 100. In order to maximize achieved amplification, horn 110 is generally circular at its point of coupling to speaker 112 and gradually becomes elliptical as it approaches its terminus 110a. The length of acoustic horn 110 is carefully selected to maximize the audible output of tones generated by speaker 112. A tuning process, an example of which is described more fully hereinafter, should thus be performed which includes testing the desired circuitry with acoustic horns of varying lengths and configurations until maximum amplitudes are achieved for given frequencies. For the preferred embodiment for the present invention, horn 110 should have an acoustic length of between about 1.50 and 2.75 inches, preferably about 1.75 and 2.25 inches.

The larynx of the present invention is controlled by bridging anterior contacts 114, or posterior contacts 116 with the tongue. As is described more fully hereinafter, the touching of either of these pairs contacts acts to complete a ground path in the artificial larynx. Anterior contacts 114 provide a pause control which instantaneously interrupts the generation of sound by the larynx for as long as the contacts are bridged. The posterior contacts 116 is provide an on-off control which must be touched by the tongue for a pre-selected period of time. By requiring prolonged tongue contact of posterior contacts 116, inadvertent switching between the off and on positions is effectively prevented. The efficiency of the sound circuitry makes it possible to use a low-voltage, low-current power source, such as batteries 118. For the embodiment shown in FIG. 1, these batteries may be entirely sealed within the dental prosthesis 100, and may be of the lithium, silver oxide, or nickel cadium type. In alternate embodiments replacement of such batteries may be permitted. It is presently preferred to provide a solar cell 120 which is located within the dental prosthesis adjacent to an area of transparent material in that prosthesis. The current drain of the larynx of the present invention is sufficiently low as to facilitate recharging of the larynx on a periodic basis by removing the larynx and replacing it under an artificial light source, such as incandescent light.

Special precautions are taken to prevent speaker 112 from becoming fouled with water or saliva. In addition to increasing the amplitude sound generated by speaker 112 acoustic horn 110 aids in protecting speaker 112 from liquids contained within the mouth. This protection results from the location of the speaker at the proximate end of the horn, and is further enhanced through the provision of a mesh 122 which is located at the speaker orifice. Applicants have found that introduction of saliva or water into acoustic horn 110 is unlikely, and that such amounts as may be introduced to acoustic horn 110 are effectively shielded from speaker 112 by mesh 122. Mesh 122 does not appreciably interfere with sound transmission from the speaker 112 to horn 110.

FIG. 1 diagrammatically illustrates representative mountings of solar cell 120, battery 118, sound generation circuitry 124, speaker 112, mesh 122, contacts 114 and 116, and acoustic horn 110. FIG. 2 provides further information concerning the operation of the preferred embodiment larynx of the present invention. In FIG. 2, further details of the sound generation and switching circuitry are provided. As a matter of illustrative convenience, batteries 118 and solar cell 120 are not illustrated in FIGS. 2 or 3. FIG. 3 is a circuit diagram providing the details of the circuit which is diagrammatically illustrated in FIG. 2. Portions of the circuit illustrated in FIG. 3 which correspond to blocks illustrated in FIG. 2 are surrounded by similarly numbered dotted outlines.

Referring now to FIGS. 2 and 3, the signal generation circuitry of the present invention is seen to comprise a signal generator 200 and differentiator 202. In the preferred embodiment, a square wave signal generator is utilized, the resultant signal of which is differentiated to produce an output signal comprising a plurality of spikes which are separated by long near-zero voltage time periods. In the preferred embodiment, the square wave signal generator comprises an astable multivibrator which generates a signal having a frequency between 0 and 20 KHz preferably 60 Hz for males and 120 Hz for females. By differentiating the signal generator output, the frequency and maximum amplitudes of the positive and negative spikes produced thereby will, of course, correspond to the frequency and amplitude of the square wave signal. The periods of return to near-zero voltage between spikes of the differentiated signal are too short to be audibly resolved, and thus, an "audio flicker" is creates when the output signal is fed to audio amplifier 212, and to speaker 112 to produce the output tone of the larynx. Thus, the amplitude and frequency of the apparent sound produced by the larynx has not been changed, while the duty cycle, and thus the power drain, of the output signal has been substantially reduced. A duty cycle control means is thus provided which is utilized to reduce the duty cycle of the output of the signal generation means by profitably utilizing the audio flicker effect. In the preferred embodiment, the duty cycle of the sound generation means is at least less than 10%, generally less than 5%, and most preferably less that about 1.0%.

The preferred embodiment artificial larynx further comprises a tongue activatable intraoral switching device. This switching device comprises an on-off circuit for activating or deactivating the device. This selective enabling and disabling function is accomplished by providing a timing means for timing the closure of a switch which, in the preferred embodiment is accomplished by completion of a ground path through contacts 116. The desired grounding may be accomplished by bridging between adjacent contacts with the tongue, or by using the body as the system's ground whereby touching a single contact will accomplish a grounding of the system. In this embodiment, counter 204 counts in response to the output ($\phi$) of the signal generation means when the on-off contacts 116 are grounded, but is inhibited (through R11 in FIG. 3) from counting when the on-off contacts 116 are not grounded. In order to turn on the artificial larynx, the tongue is held against "on-off" contacts 116 until counter 204 has been permitted to count for a preselected period of time, after which an output pulse is provided to differentiator and inverter 206. The output pulse of counter 204 is thus differentiated and inverted in 206 in order to provide a distinct output to bistable multivibrator (flip-flop) device 208, which is caused to assume its "on" position. When in this position, flip-flop 208 provides a high level signal to "and" gate 210. If anterior "pause" contacts 114 are not grounded, and thus also provide a high level signal to "and" gate 210, then the differentiated output of signal generator 200 will be permitted to pass to high gain amplifier 212 and to speaker 112. When the user hears the signal from speaker 112, the tongue may be removed from on-off contact 116, and the flip-flop 208 will remain in its "on" position.

As mentioned above, pause contacts 114 are utilized to momentarily deactivate amplifier 212 and speaker 112. Under normal conditions, pause contacts 114 are open, and thus the signal to "and" gate 210 is high (through R12 in FIG. 3), permitting, in combination with a high signal from flip-flop 208, the passage of the differentiated output signal 202 to amplifier 212 and speaker 112. When the tongue is used to bridge pause contacts 114, the output drops to zero, and "and" gate 210 prevents the transfer of any signal to the amplifier and speaker.

It is anticipated that the switching device of the present invention may be utilized by a proficient user to closely approximate natural speech. The pause contact 114 may be utilized to stop any sound from being generated between sentences, or even between words.

In FIG. 3, a circuit diagram corresponding to the block diagram set forth in FIG. 2 is provided, each of the blocks of FIG. 2 being illustrated within dotted outlines surrounding its respective circuit components. Preferred components for use in constructing the preferred embodiment artificial larynx are as follows:

| Component | Vendor/Part # | Description |
|---|---|---|
| R1 | Mini-Systems MSR-2 | Resistor 2.2 Meg. |
| R2 | Mini-Systems MSR-2 | Resistor 270K |
| R3 | Mini-Systems MSR-2 | Resistor 18K |
| R4 | Mini-Systems MSR-2 | Resistor 1 Meg. |
| R5 | Mini-Systems MSR-2 | Resistor 1 Meg. |
| R6 | Mini-Systems MSR-2 | Resistor 100K |
| R7 | Mini-Systems MSR-2 | Resistor 1 Meg. |
| R8 | Mini-Systems MSR-2 | Resistor 1 Meg. |
| R9 | Mini-Systems MSR-2 | Resistor 100K |
| R10 | Mini-Systems MSR-2 | Resistor 2.7K |
| R11 | Mini-Systems MSR-2 | Resistor 10K |
| R12 | Mini-Systems MSR-2 | Resistor 10K |
| C1 | Johanson 500R15W182KP | Capacitor 0.0018 ufd |
| C2 | Johanson 500R11Y103PP | Capacitor 0.01 ufd |
| C3 | Johanson 500R11Y103PP | Capacitor 0.01 ufd |
| C4 | Johanson 500R11Y103PP | Capacitor 0.01 ufd |
| C5 | Johanson 500S48N105PP4 | Capacitor 1.0 ufd |
| D1, D2 | Amperex LDD15T | Dual Diode |
| D3 | Amperex LDD5T | Logic Diode |
| Q1 | Amperex LDA405T | NPN Transistor |
| Q2 | Amperex LDA405T | NPN Transistor |
| Q3 | Amperex LDA405T | NPN Transistor |
| Q4 | Amperex LDA453T | PNP Transistor |
| SP1 | Knowles BK-1610 | Speaker |
| IC1 | Amperex LFG4011 | Quad 2 input NAND |
| IC2 | Amperex LFC4020 | 14 Stage Binary Counter |
| S1 | — | Silver Contacts |
| S2 | — | Silver Contacts |
| B1 | Sanyo CR1220 | Lithium Battery 3 v |
| B2 | Sanyo CR1220 | Lithium Battery 3 v |

One of ordinary skill in this art will readily appreciate that while a signal generator of frequencies of 70 and 120 Hz have been selected for use in the disclosed artificial larynx, other frequencies and/or dual frequencies may be provided to accommodate individual preferences. Similarly, connections to pins Q7 and Q8 of binary counter IC2 provide the aforementioned two second and four second on-off times. Other combinations of connections Q1–Q14 may be used to speed, slow, or otherwise alter the relative on-off times of the preferred embodiment device.

As mentioned above, it is preferred to provide an acoustic amplification means for amplifying acoustic energy within the oral cavity. It is further desired to tune the acoustic amplification means to the sound source to maximize the amplification. Accordingly, tests have been conducted to demonstrate the effectiveness of a horn to amplify the output of a speaker of the type preferred for use in the artificial larynx of the present invention. In one set of tests, the output of a BK1610 speaker was fed into a horn. The output from the horn was compared to the output of a similar BK1610 speaker, sound measurements being taken using a Scott type 451 (A weighted) sound meter. At 80 Hz, the speaker with horn generated a 57 decibel tone, by comparison to a 51 decibel tone generated by the speaker without a horn. At 120 Hz a 60 decibel output was achieved with the horn and a 53 decibel output without the horn. At combined input frequencies of 80 and 120 Hz, a 62 decibel output was achieved with the horn, and a 54 decibel output achieved without the horn. These changes are quite significant. A 6 decibel change indicates twice the pressure level, while a 10 decibel change indicates that the sound is perceived as being twice as loud.

In order to further investigate the effect of different horn lengths, a study was undertaken to determine the optimal length using a 1½ volt circuit powering a BK1610 speaker. This speaker was placed at varying distances from the diaphram of a sound level meter, to ascertain the optimal length for an acoustic horn. Ambient sound accounted for 40 decibels under "no signal" conditions. Lengths of between ¾ of an inch and 9¼ inches were tested, with maximum vales of 98 decibels being obtained for 1¾ and 2 inch lengths. This testing is set forth in Table I:

TABLE I
DECIBELS vs. HORN LENGTH

| | |
|---|---|
| 95 | 9.25 |
| \| | \| |
| 95 | 7.5 |
| 96 | 7.25 |
| \| | \| |
| 96 | 5.5 |
| 95 | 5.0 |
| 94 | 4.75 |
| \| | \| |
| 94 | 4.0 |
| 95 | 3.75 |
| \| | \| |
| 95 | 3.0 |
| 96 | 2.75 |
| 96 | 2.5 |
| 97 | 2.25 |
| 98 | 2.0 |
| 98 | 1.75 |
| 96+ | 1.5 |
| 95 | 1.25 |
| 95 | 1.0 |
| 94 | .75 |

Although the results set forth in Table I were obtained using a straight, cylindrical horn, the above-described tests were repeated using an arcuate, elliptical horn, and comparable results were obtained. It should further be noted that the circuitry used to drive the speaker in the tests referred to above was early prototype circuitry which failed to comprise any duty cycle control means.

One of ordinary skill in the art will appreciate that the voltage of the preferred embodiment device may also be varied, and that with such variations, some variation in loudness will be obtained. Using the preferred embodiment circuitry of the present invention, it has been found that a decibel output of between about 91 and 111 decibels may be obtained using different values for resistor R10 in section 212. Table II, which is set forth below, provides information concerning current drain for both conditions of 'device on' and 'device off' and the decibel output for different values of R10.

TABLE II

| CURRENT DRAIN VS. LOUDNESS FOR DIFFERENT VALUES OF R10 | | | |
|---|---|---|---|
| R10 (KILOHMS) | DEVICE CURRENT 'ON STATE' (ma) | DEVICE CURRENT 'OFF STATE' (ma) | LOUDNESS (db) |
| (SUPPLY VOLTAGE = 6.0 VOLTS) | | | |
| 1 | 4.05 | 0.15 | 110.5 |
| 1.5 | 2.93 | \| | 110 |
| 2.2 | 2.18 | \| | 109 |

TABLE II-continued

CURRENT DRAIN VS. LOUDNESS FOR DIFFERENT VALUES OF R10

| R10 (KILOHMS) | DEVICE CURRENT 'ON STATE' (ma) | DEVICE CURRENT 'OFF STATE' (ma) | LOUDNESS (db) |
| --- | --- | --- | --- |
| 3.3 | 1.59 | | 108 |
| 4.7 | 1.21 | | 106.5 |
| 5.6 | 1.05 | | 105.5 |
| 6.8 | 0.91 | | 104 |
| 7.5 | 0.84 | | 103.5 |
| 10 | 0.68 | | 101.5 |
| 15 | 0.51 | | 98.5 |
| (SUPPLY VOLTAGE = 3.0 VOLTS) | | | |
| 1. | 1.54 | 0.14 | 103 |
| 1.5 | 1.12 | | 101.5 |
| 1.8 | 0.98 | | 101 |
| 2.2 | 0.84 | | 100 |
| 2.7 | 0.72 | | 99 |

As seen from the above, depending upon the loudness and the current drain desired, different values of amplifier resistor R10 may be provided to power the preferred embodiment larynx of the present invention.

While discrete electronic components are described above, one of ordinary skill in the art will readily appreciate that most of the disclosed circuit components can be included in a single semiconductor chip, and that such a chip is preferred for construction of the preferred embodiment of the present invention.

As seen from the above, a highly efficient wholly self contained artificial larynx is described which overcomes many of the disadvantages of prior art devices.

We claim:

1. An intraoral artificial larynx, comprising:
   (a) prosthetic means for mounting said larynx within the oral cavity;
   (b) a power source mounted on said prosthetic means;
   (c) signal generation means mounted on said prosthetic means for generating a preselected electrical signal;
   (d) speaker means mounted on said prosthetic means for converting said signal into acoustic energy; and
   (e) a tongue activatable intraoral switch mounted on said prosthetic means; said switch comprising a contact for completing a ground path of said larynx through the tongue.

2. An intraoral artificial larynx, comprising:
   (a) prosthetic means for mounting said larynx within the oral cavity;
   (b) a power source mounted on said prosthetic means;
   (c) signal generation means mounted on said prosthetic means for generating a preselected electrical signal;
   (d) speaker means mounted on said prosthetic means for converting said signal into acoustic energy; and
   (e) a tongue activatable intraoral switch means comprising a first on-off switch for selectively enabling and disabling at least said speaker means; and comprising a second disabling switch for momentarily disabling at least said speaker means.

3. An intraoral artificial larynx, comprising:
   (a) prosthetic means for mounting said larynx within the oral cavity;
   (b) a power source mounted on said prosthetic means;
   (c) signal generation means mounted on said prosthetic means for generating a preselected electrical signal;
   (d) speaker means mounted on said prosthetic means for converting said signal into acoustic energy; and
   (e) a tongue activatable intraoral switch means mounted on said prosthetic means comprising an on-off switch for selectively enabling and disabling at least said speaker means, said switch means further comprising a timer means for timing the closure of said on-off switch to enable said speaker means in response to the timed closure of said switch.

4. The invention of claim 3 wherein said timer means disables said speaker means in response to the timed closure of said on-off switch.

* * * * *

UNITED STATES PATENT AND TRADEMARK OFFICE
CERTIFICATE OF CORRECTION

PATENT NO. : 4,502,150

DATED : February 26, 1985

INVENTOR(S) : Philip Katz, Henry S. Brenman, Louis D. Lowry
Harold Schwartz

It is certified that error appears in the above-identified patent and that said Letters Patent is hereby corrected as shown below:

Column 1, line 25, please delete "whle" and substitute therefor --while--.

Column 6, line 9, please delete "creates" and substitute therefor --created--.

Column 8, line 13, please delete "vales" and substitute therefor --values".

Signed and Sealed this

Thirtieth Day of July 1985

[SEAL]

Attest:

DONALD J. QUIGG

*Attesting Officer*  *Acting Commissioner of Patents and Trademarks*